United States Patent [19]

Speckman

[11] Patent Number: 4,562,794
[45] Date of Patent: Jan. 7, 1986

[54] PEST CONTROL IN ANIMALS

[75] Inventor: Calvin A. Speckman, Bend, Oreg.

[73] Assignee: Bend Research, Inc., Bend, Oreg.

[21] Appl. No.: 575,002

[22] Filed: Jan. 30, 1984

[51] Int. Cl.⁴ .............................................. A01K 13/00
[52] U.S. Cl. ..................................................... 119/156
[58] Field of Search ......................................... 119/156

[56] References Cited

U.S. PATENT DOCUMENTS

| | | | |
|---|---|---|---|
| 3,756,200 | 9/1973 | Ohlhausen | 119/156 |
| 3,949,708 | 4/1976 | Meeks | 119/156 |
| 4,189,467 | 2/1980 | von Bittera et al. | 119/156 X |
| 4,366,777 | 1/1983 | Akhavein et al. | 119/156 |
| 4,425,874 | 1/1984 | Child | 119/156 |

Primary Examiner—Hugh R. Chamblee
Attorney, Agent, or Firm—Chernoff, Vilhauer, McClung, Birdwell & Stenzel

[57] ABSTRACT

A device and method for the control of animal pests, especially ectoparasites on livestock and poultry, is disclosed. The device comprises (1) a tag element, and (2) a replaceable controlled-release dispenser element, the latter dispensing an active ingredient at a zero-order rate of release over a period of several months. The dispenser comprises an active ingredient reservoir and a rate-controlling membrane, the reservoir having interconnected pores and being capable of retaining the active ingredient by capillary forces. The method comprises releasing active ingredient in close proximity to the animal's body by means of a device of the type described.

22 Claims, 5 Drawing Figures

PEST CONTROL IN ANIMALS

BACKGROUND OF THE INVENTION

This invention relates to a device and method for controlling pests in animals, especially livestock and poultry.

A longstanding problem that has plagued the livestock and poultry industries is the existence of ectoparasitic and disease-carrying pests such as face flies, stable flies, horn flies, Gulf Coast ticks, Spinose ear ticks, fleas, mites, chiggers, and screw worms. Other types of pests, namely predators such as coyotes, foxes, cougars, bobcats, etc., have been troublesome as well. Numerous attempts have been made to control such pests, but all have practical or economic disadvantages. For example, sprays, dusts and dips have been used for some time with varying degrees of success, but application is often labor intensive and protection is usually of short duration.

Livestock eartags comprising a composite polymer with pesticide or repellent dispersed thereon or therein are known. See, for example, U.S. Pat. Nos. 3,756,200, 3,942,480, 3,949,708, 4,059,074, and 4,195,075. However, such devices suffer from various disadvantages, such as not being reusable; of having a release rate which is nonzero order or declining over time, nonadjustable and of relatively short duration; of insufficient tensile and ductile strength which contributes to brittleness, thus causing loss through breakage; and, in some cases, toxicity to the livestock. Further, nonzero order or a declining rate of release over time is wasteful and often allows target insecttype pests to develop immunity to the pesticide.

Eartags with replaceable active ingredient dispensers are also known. See, for example, U.S. Pat. No. 4,366,777 which discloses a dispenser comprising a strip of polymeric tape with either an activeingredient-soaked wick or an active-ingredient-impregnated polymeric layer attached thereto, the strip capable of encircling the neck portion of an eartag and either adhering to itself by pressure-sensitive adhesive or threading through itself in the same manner as a garbage-bag-style tie. The wick may be a fibrous sleave soaked by a crushable ampoule containing the active ingredient. However, such dispensers suffer from some of the same drawbacks as other prior art attempts at pest control, i.e., having a release rate which is non-zero order, nonadjustable, and of relatively short duration.

There is therefore a need for a pest control which is effective and inexpensive, durable, reusable, adjustable, and has a long-term zero-order release rate of pesticide or repellent. These needs and others have been met by the novel device and method of the present invention, which are summarized and particularly described below.

SUMMARY OF THE PRESENT INVENTION

There are two aspects to the present invention. One comprises a device for the control of pests in animals, especially livestock and poultry, the device comprising (1) a durable attachment element suitable for attachment either directly to or in close proximity with the animal's body, and (2) a replaceable controlled-release dispenser element, the dispenser element comprising (a) a porous reservoir having interconnected pores with pesticide or repellent dispersed and retained therein by capillary forces, and (b) a rate-controlling membrane capable of releasing the pesticide or repellent therethrough by diffusion.

The other aspect of the present invention comprises a method for controlling pests in animals, the method comprising dispensing, at a zero-order pesticidally-or repellent-effective rate of release essentially all of a pesticide or repellent contained in a porous reservoir having interconnected pores, the dispensation being accomplished by attaching, either directly or in close proximity to the animal's body, a controlled-release dispenser of the above description.

DETAILED DESCRIPTION OF THE INVENTION

As mentioned above, the device of the present invention comprises an attachment element and a controlled-release dispenser element.

The attachment element may be in any suitable form known in the art for attaching either directly to some part of the animal's body or to commonly-used animal equipment such as collars, halters, saddles, etc. For example, it may be a tag or band attachable directly to the animal's body by crimping, as in the case of a cattle tail tag or a poultry legband; by barbed spikes or rivet-punching, as in the case of a livestock eartag; by weaving into the animal's hair, for example, in the mane or tail of a horse; by a ring; by a buckle, as in the case of a pet collar; or by looping and snapping. It may be attached to equipment by any of the same methods or combinations thereof, the only constraint being that the method of attachment not interfere with the release of active ingredient.

The tag or band itself may be constructed of a suitable durable material such as metal, fabric, or high-tensile-and-ductile-strength polymers, the requirements being sufficient strength and flexibility so as to withstand weathering and the animal's day-to-day activities and attempts to remove it.

Figure 1:
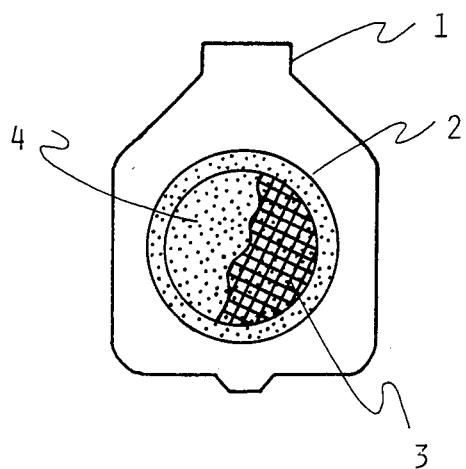
FIG. 1 is a partially cutaway schematic view in plan of an exemplary combination tab/controlled-release dispenser of the present invention.
Figure 2:
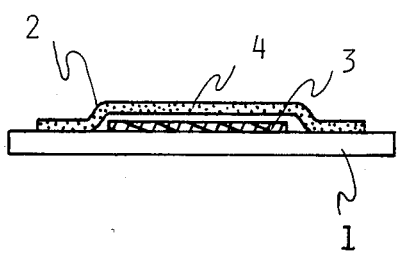
FIG. 2 is a cross-sectional view of the same device shown in FIG. 1.
Figure 5:
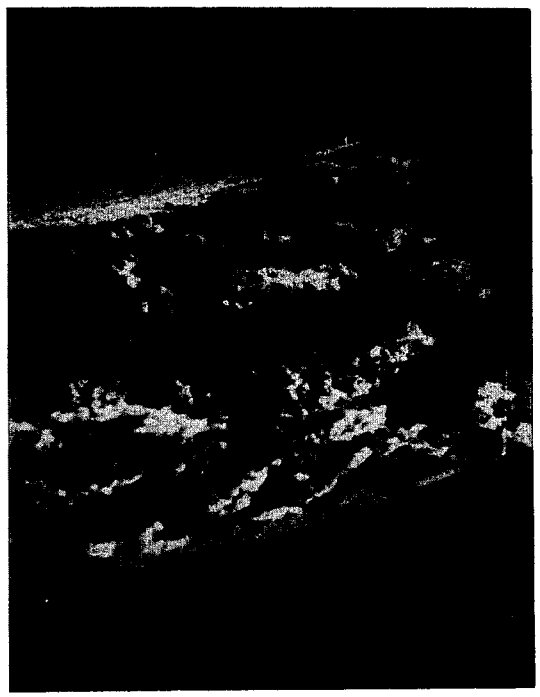
FIG. 5 is an electron microscope photograph of a cross section of the interconnected pores of the reservoir material of the controlled-release dispenser element of the device of the present invention.

Referring now to the drawings, wherein identical numbers designate like elements, FIGS. 1 and 2 show an animal tag 1 in combination with a controlled-release dispenser 2 having a reservoir 3 with interconnected pores of the type shown in FIG. 5 and a membrane 4 capable of releasing active ingredient by diffusion at a zero-order rate of release over a period of several months to a year, or more, the membrane 4 being sealed over the reservoir 3 and at its edges over tag 1, thus also serving to hold the dispenser in place.

Figure 3:
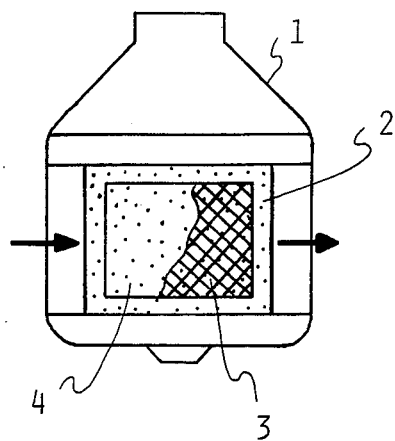
FIG. 3 is a partially cutaway schematic view in plan of another exemplary device of the present invention with a removable or replaceable controlled-release dispenser insert.
Figure 4:
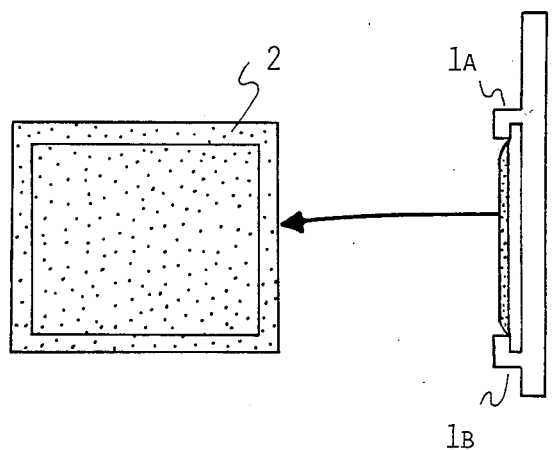
FIG. 4 is a cross-sectional view of the same device shown in FIG. 3.

A similar device with a replaceable controlled-release dispenser insert is shown in FIGS. 3-4, the tag 1 having raised channels 1a and 1b for accepting controlled-release inserts 2. With such a device there is no need to remove or replace the tag itself, which is expensive from a labor standpoint and an otherwise difficult task from the standpoint of isolating the animal and finding an appropriate place on its body for attachment.

Other means of attaching the controlled-release insert to the tag element include gluing, snap-tight fitting, riveting, and peel-off pressure-sensitive adhesive tape. The controlled-release dispenser insert may be attached to already-existing tags by any of the same means, thus avoiding the need to reattach new bands or tags.

The porous reservoir portion of the controlled-release dispenser of the present invention is formulated preferably from porous polysulfones, nylons, polycarbonates, polyvinylidene chloride, polyvinylidene fluoride, polytetrafluoroethylene, cellulose esters, regenerated cellulose, polyolefins, polyurethanes, cross-linked polyvinyl alcohols, epoxy resins, and polyvinyl chlorides having interconnected pores of the type shown in FIG. 5, the pores being appropriate in size to retain the active ingredient in liquid or solid form in the reservoir by capillary action.

The reservoir material is prepared by conventional wet casting/evaporation techniques known in the art.

The reservoir material should be such that the active ingredient is essentially insoluble in the reservoir. In the case of solid active ingredients, the solid is preferably transformed into a liquid by melting or by dissolving or dispersing in a liquid, and this liquid is retained by the porous reservoir by capillary action until it solidifies. A typical actual cross section of the reservoir material showing its interconnected pores is shown in FIG. 5, which is an electron microscope photograph of such a cross section magnified 700 times. In this manner, the only forces retaining the active ingredient in the reservoir are physical, rather than chemical forces such as would be the case if the active ingredient forces were appreciably soluble in the reservoir. In the latter case, much of the active ingredient is prevented from being released at zero-order rates.

The release rate of the active ingredient through the rate-controlling membrane can be conveniently adjusted to the desired value by techniques known in the art including varying the surface area, thickness and composition of the membrane. Exemplary materials for fabricating the polymeric membrane include polyethylene; polypropylene; polytetrafluoroethylene; ethylene/vinyl acetate copolymers; silicone rubbers; neoprene rubber; chlorinated polyethylene; polyvinyl chlorides, vinyl chloride copolymers with vinyl acetate, vinyllidene chloride, ethylene, and propylene; polyethylene terephthalate; butyl rubber; epichlorohydrin rubbers; ethylene/vinyl alcohol copolymers; polystyrene/acrylonitrile copolymers; polyamides; polyurethanes; polyesters; and the like.

The invention is particularly useful for the controlled release of liquid active ingredients. Controlled-release dispensers that contain liquids are difficult to fabricate without a solid reservoir. The use of porous reservoirs that hold the active ingredient by capillary action thus enables easy fabrication of dispensers of liquid active ingredients. Exemplary pesticides and repellents which are effective against horn flies, face flies, stable flies, house flies, mosquitoes, lice, ticks, and mites are bioresmethrin, permethrin, tetramethrin, cypermethrin, decamethrin, pyrethrins, resmethrin, cyhalothrin, allethrin, dichlorvos, carbaryl, naled, citrus oils, citronella oil, pine oil, stirofos, fenvalerate, stabilene, benzyl benzoate, methyl nonyl ketone, N-butylacetanilide, di-n-propyl isocinchomeronate, 2-octylthioethanol, dimethyl carbate, dimethyl phthalate, N,N-diethyl-m-toluamide, and 2,3:4,5-bis (2-butylene)-tetrahydro-2-furfural. Many of these active ingredients are effective both as a pesticide and a repellent, and the activity of many is enhanced by the inclusion of a synergist. Especially preferred synergists include piperonyl butoxide and N-octyl bicycloheptene dicarboximide.

The active ingredient may also be a repellent or poison effective against predatory animals such as coyotes, foxes, dogs, cats, cougars, bobcats, and the like.

The active ingredient may have a coloring agent added thereto so as to indicate the amount thereof remaining. Some active ingredients are sensitive to degradation by oxidation or by ultraviolet light, and must be protected in order to provide long-term action. The invention is particularly useful for providing such protection. If the active ingredient is photosensitive or especially susceptible to rapid oxidation, the reservoir or the rate-controlling membrane may contain additives such as ultraviolet light absorbers and antioxidants.

The dispenser may have a portion of its outer surface covered with an impermeable backing material so as to cause the active ingredient to be released, in the case of a disc shape, from one side only. A suitable impermeable backing film is a polyethylene-foil-paper laminate made by Lithotype Co. of South San Francisco, Calif. In some cases, as in the case of a polyurethane rate-controlling membrane, the polyetheneside backing of the film must first be coated with an adhesive such as Elvax 40 made by DuPont.

The membrane may be clear so as to provide visual observation of the active ingredient or it may be color coded to indicate ownership, release rate, type of active ingredient, or date of attachment to the animal. Coloring may also extend the life of the dispenser by shielding the active ingredient and the polymeric membrane itself from ultraviolet light.

EXAMPLE 1

Devices of the invention were prepared using the following components:
  Attachment device: polyurethane cattle ear tag
  Porous reservoir: cellulose filter material, grade 113 (Whatman Laboratory Products of Clifton, N.J.), 5-cm diameter
  Membrane: polyurethane, Tuftane 310 (Lord Corporation of Erie, Pa.), 15 mils thick, 7.5-cm diameter
  Active ingredient: cypermethrin, 2 g The devices were prepared by the following procedure: the porous reservoir was placed on the attachment device and the active ingredient was dispensed onto the reservoir with a pipette. The membrane was then placed over the filled reservoir and was sealed to the attachment device on its perimeter using a circular heat sealer. Total releasing surface area was 29 $cm^2$. These devices were attached to the ears of cattle and were observed to protect the cattle from ticks for at least three months.

EXAMPLE 2

Devices were prepared as in Example 1 with the exception that the active ingredient was a mixture of 1 g each permethrin and piperonyl butoxide. These devices were attached to the ears of cattle and protected the cattle from face flies for longer than three months.

EXAMPLE 3

Devices were prepared as in Example 2 with the exceptions that a reservoir, active ingredient, and membrane were affixed to each side of each device, the total quantity of active ingredients was 1 g on each side of the device, and the membrane thickness was 5 mils. These devices were attached to cattle and were observed to protect cattle from ticks for at least three months.

EXAMPLE 4

Devices were prepared as in Example 1 with the exception that the active ingredient was deltamethrin, which was dispersed in corn oil (2 g deltamethrin in 0.7 g corn oil) to render it a liquid.

EXAMPLE 5

Devices were prepared as in Example 2 with the exception that the reservoir material was microporous polysulfone of the type shown in FIG. 5 (magnified 700×) prepared by casting a 10% by weight solution of polysulfone (made by Union Carbide of New York, N.Y. and sold under the trade name Udel P-1700) in dimethyl formamide. The solution was cast 20 mils thick on a glass plate and immediately immersed in a room temperature water bath, which precipitated the polysulfone in the desired formulation. The polysulfone sheet was dried at 110° for an hour and a reservoir was cut therefrom with a circular punch. These devices were attached to cattle and were observed to protect cattle from face flies for longer than three months.

EXAMPLE 6

Devices of the invention were prepared using the following components:
  Attachment device: polyurethane cattle ear tag
  Porous reservoir: polypropylene mesh, 3.2-cm diameter
  Membrane: polyurethane, Tuftane 310, 17 mils thick, black color, 5-cm diameter
  Active ingredient: 1 g permethrin +1 g piperonyl butoxide
  Impermeable backing: laminated polyethylene/aluminum foil/polyethylene/paper, 4.1-cm diameter The following procedure was used to prepare the devices: the reservoir was placed on the impermeable backing, and the active ingredient was dispensed onto the reservoir with a pipette. The membrane was then placed over the filled reservoir and was sealed to the impermeable backing on its perimeter using a heat sealer. The total releasing surface area was 9 cm². This controlled-release dispenser was then placed onto the attachment device and was sealed to the device on its perimeter using a sonic welder.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A device for the control of pests on an animal comprising attachment means attachable either directly or in close proximity to the body of said animal and a controlled-release dispenser capable of dispensing essentially all of an active ingredient comprising a pesticide or repellent contained in said dispenser at a zero-order effective rate of release, said dispenser comprising a membrane controlling the rate of release of said active ingredient by diffusion through said membrane, and a porous reservoir material which is highly permeable to said active ingredient and in which said active ingredient is essentially isoluble, said porous reservoir material having interconnected pores capable of retaining said active ingredient by capillary forces, said dispensation of active ingredient taking place through said rate-controlling membrane by diffusion, and said rate-controlling membrane forming a continuous surface over said porous reservoir material and sealed at the edges thereof.

2. The device of claim 1 wherein the ratecontrolling membrane is selected from polymers and copolymers of ethylene, propylene, tetrafluoroethylene, ethylene/ethyl acrylate, ethylene/vinyl acetate, chlorinated ethylene, vinyl chloride, vinyl chloride/vinyl acetate, vinylidene chloride, ethylene terephthalate, ethylene/vinyl alcohol, ethylene/vinyl acetate/vinyl alcohol, ethylene/vinyloxyethanol, and styrene/acrylonitrile; rubbers of silicone, neoprene, butyl, and epichlorohydrin; polycarbonate; polyamides and polyimides; polyurethanes; and polyesters.

3. The device of claim 1 wherein the rate-controlling membrane is a polymer selected from polyethylenes, polyurethanes, polyesters, polyamides, polycarbonates, and vinyl polymers.

4. The device of claim 1 wherein the porous reservoir material is selected from polysulfones, polytetrafluoroethylene, polycarbonates, polyurethanes, polyethylenes, polypropylenes, and cellulosic materials.

5. The device of claim 1 additionally containing antioxidants, ultraviolet light absorbers, and/or coloring agents.

6. The device of claim 1 wherein a portion of the outer surface of the device is covered with a material that is essentially impermeable to the active ingredient.

7. The device of claim 1 wherein said active ingredient comprises at least one insecticide selected from the group consisting essentially of synthetic pyrethroids, pyrethrins, organophosphates, carbamates, and organochlorides.

8. The device of claim 1 wherein said active ingredient comprises at least one insect repellant selected from the group consisting essentially of aromatic esters, organic amides and natural oils.

9. The device of claim 1 wherein said active ingredient is selected from one or more of benzyl benzoate, di-n-propyl isocinchomeronate, dimethyl carbate, dimethyl phthalate, N-butylacetanilide, N,N-diethyl-m-toluamide, citrus oils, citronella oil, pine oil, methyl nonyl ketone, 2-octylthioethanol and 2,3:4,5 bis (2-butylene)-tetrahydro-2-furfural.

10. The device of claim 1 wherein the attachment means is a tag and the controlled-release dispenser is replaceable.

11. The device of claim 10 wherein the tag is an ear-tag.

12. The device of claim 1 wherein said active ingredient comprises one or more of bioresmethrin, permethrin, cypermethrin, decamethrin, tetramethrin, allethrin, pyrethrins, resmethrin, cyhalothrin, fenvalerate, stirofos, citrus oils, naled, carbaryl, and dichlorvos.

13. The device of claim 12 wherein said active ingredient includes a synergist.

14. The device of claim 13 wherein said synergist is piperonyl butoxide.

15. A method of controlling pests on an animal comprising dispensing in close proximity to said animal's body at a zero-order effective rate of release an active ingredient comprising a pesticide or repellent comprising loading a porous reservoir material with said active ingredient, said porous reservoir material being highly permeable to said active ingredient and in which said active ingredient is essentially insoluble, said porous reservoir material having interconnected pores capable of retaining said active ingredient by capillary forces, and releasing said active ingredient by diffusion through a rate-controlling membrane, said rate-controlling membrane forming a continuous surface over said porous reservoir material and sealed at the edges thereof.

16. The method of claim 15 wherein the ratecontrolling membrane is a polymer selected from polyethylenes, polyurethanes, polyesters, polyamides, polycarbonates, and vinyl polymers.

17. The method of claim 15 wherein the porous reservoir material is selected from polysulfones, polytetrafluoroethylene, polycarbonates, polyurethanes, polyethylenes, polypropylenes, and cellulosic materials.

18. The method of claim 15 additionally comprising heating said active ingredient together with said reservoir and said membrane prior to releasing said active ingredient by diffusion through said rate-controlling membrane.

19. The method of claim 15 additionally comprising random periodic contact of said active ingredient with said animal's body.

20. The method of claim 15 wherein said active ingredient is selected from one or more of permethrin, cypermethrin, tetramethrin, allethrin, decamethrin, pyrethrins, resmethrin, cyhalothrin, fenvalerate, stirofos, citrus oils, naled, carbaryl, and dichlorvos.

21. The method of claim 20 wherein said active ingredient further comprises a synergist.

22. The method of claim 21 wherein said synergist is piperonyl butoxide.

* * * * *

UNITED STATES PATENT AND TRADEMARK OFFICE
CERTIFICATE OF CORRECTION

PATENT NO. : 4,562,794

DATED : January 7, 1986

INVENTOR(S) : Calvin A. Speckman

It is certified that error appears in the above-identified patent and that said Letters Patent is hereby corrected as shown below:

| | |
|---|---|
| Col. 1, Line 33 | Change "insecttype" to --insect-type-- |
| Col. 1, Line 38 | Change "activeingredient-soaked" to --active-ingredient-soaked-- |
| Col. 2, Line 15 | Change "tab/controlled-release" to --tag/controlled-release-- |
| Col. 4, Line 38 | Change "polyethyleneside" to --polyethylene-side-- |
| Col. 6, Line 8 | Change "isoluble" to --insoluble |
| Col. 6, Line 16 | Change "ratecontrolling" to --rate-controlling-- |
| Col. 7, Line 19 | Change "ratecontrolling" to --rate-controlling-- |

Signed and Sealed this

Thirtieth Day of September 1986

[SEAL]

Attest:

DONALD J. QUIGG

Attesting Officer

Commissioner of Patents and Trademarks